United States Patent [19]

Yamamoto

[11] Patent Number: 5,773,410
[45] Date of Patent: Jun. 30, 1998

[54] METHOD FOR PURIFYING (−)-N-ISOPULEGOL AND CITRUS PERFUME COMPOSITION CONTAINING (−)-N-ISOPULEGOL OBTAINED BY THE METHOD

[75] Inventor: Takeshi Yamamoto, Kanagawa, Japan

[73] Assignee: Takasago International Corporation, Tokyo, Japan

[21] Appl. No.: 506,356

[22] Filed: Jul. 24, 1995

[30] Foreign Application Priority Data

Jul. 29, 1994 [JP] Japan .................................. 6-196282

[51] Int. Cl.$^6$ .......................................... A61K 7/46
[52] U.S. Cl. .................................................. 512/23
[58] Field of Search ...................................... 512/23

[56] References Cited

U.S. PATENT DOCUMENTS

| | | | |
|---|---|---|---|
| 4,217,371 | 8/1980 | Sprecker et al. | 426/538 |
| 5,545,424 | 8/1996 | Nakatsu et al. | 426/536 |

OTHER PUBLICATIONS

Lund et al., "Composition of Rough Lemon Leaf Oil", Journal of Agricultural and Food Chemistry, pp. 490–494, 1981.

Nakagawa et al., translation of JP 06–65023, Mar. 1994.

Sully et al. "The Optical Rotation of Citronellal", Perfumery and Essential Oil Record, 59, No. 5, pp. 365–366 (May 1968).

*Primary Examiner*—Jeffrey Mullis
*Attorney, Agent, or Firm*—Sughrue, Mion, Zinn, Macpeak & Seas, PLLC

[57] ABSTRACT

A method for purifying isopulegol is disclosed, comprising deep cooling isopulegol mainly composed of (−)-n-isopulegol in a solvent for deep cooling mainly comprising acetone to obtain (−)-n-isopulegol having a chemical purity of not less than 99.7% by weight and an optical purity of not less than 99.7%e.e. The thus purified (−)-n-isopulegol is odorless and gives a feeling of freshness, crispness and coolness to a citrus perfume composition.

2 Claims, No Drawings

METHOD FOR PURIFYING (−)-N-ISOPULEGOL AND CITRUS PERFUME COMPOSITION CONTAINING (−)-N-ISOPULEGOL OBTAINED BY THE METHOD

FIELD OF THE INVENTION

This invention relates to a purification method for obtaining odorless and chemically and optically pure (−)-n-isopulegol which gives a feeling of freshness, crispness, and coolness to the fragrance of a perfume composition and to a citrus perfume composition containing the thus purified (−)-n-isopulegol.

BACKGROUND OF THE INVENTION

Industrial preparation of isopulegol mainly composed of the (−)-n-compound comprises cyclization of (+)- citronellal. (+)-Citronellal (optical purity: 80 to 85%e.e.) obtained from citronella oil has conventionally been used as the starting material but recently been being replaced with optically purer (+)-citronellal (optical purity: 97.5%e.e.; see Indo Motoichi, Koryo, No. 177, pp 33–47 (1993), hereinafter referred to as "Takasago Process") obtained by asymmetric isomerization of geranyl diethylamine using an Rh-BINAP complex catalyst (Rh complex having 2,2'-bis (diphenylphosphino)-1,1'-binaphthyl as a ligand).

It is known that cyclization of (+)-citronellal is carried out by using silica gel (U.S. Pat. No. 3,218,361), zeolite (Applied Catalyst, Vol. 47, pp. 367–374 (1989)), a rhodium complex (Chem. Pharm. Bull., Vol. 37, pp. 1990–1994 (1989) and Tetrahedron Lett., pp. 4375–4376 (1972)), a copper-chromium catalyst (Bull. Chem. Soc. Jap., Vol. 41, pp. 2530–2532 (1968)), an alkylaluminum chloride (J. Am. Chem. Soc., Vol. 102, pp. 7951–7953 (1980)), a solid acid-base catalyst (Chem. Lett., pp. 1797–1798 (1989)), or zinc bromide (Japanese Patent Publication (JP-B) No. 59-45661) and Synthesis, Vol. 2, pp. 147–148 (1978)). Of these cyclization processes, the process of using silica gel has hitherto been used, while the process of using zinc bromide has recently been replacing for the high selectivity to the (−)-n- compound.

Isopulegol mainly composed of the (−)-n-compound (l-isopulegol) has a minty, herbaceous and bitter sweet odor and gives off a bitter but sharp note at a concentration of 50 ppm or higher and a herbaceous bitter note or a bitter sweet and minty note at a concentration of about 10 ppm. In the field of perfumery, it has been added to a perfume composition in a small amount for the purpose of lifting a rose note, a geranium note, a reseda note, an oriental note, a tuberose note, etc. (S. Arctander, Perfume and Flavor Chemicals, Compound No. 2768). However, there is no report of use of isopulegol in citrus perfume compositions because the fragrance of conventionally available isopulegol does not agree with a citrus note, and addition of isopulegol causes loss of the citrus note of a citrus perfume composition.

With respect to a feeling of coolness of (−)-n- isopulegol, H. Yamazaki, et al. report in Korvo, No. 95, pp. 39–43 (1970) that (−)-n-isopulegol slightly gives a feeling of coolness, though making no mention of fragrance, chemical purity or optical purity. An unexamined published Japanese patent application (JP-A) No. 6-65023) discloses applicability of (−)-n-isopulegol as an agent for giving a feeling of coolness. However, no mention of the fragrance of (−)-n-isopulegol still less use of (−)-n-isopulegol in citrus perfume compositions is found in these reports.

With the recent tendency to diversity of perfumery products, development of new perfume material excellent in various physical properties, such as safety, stability, preference, freshness, and a natural feeling, as well as quality of odor. A citrus note is one type of odors which meets all the public taste irrespective of sex and age and has been used widely, and it has been demanded to develop a compound which further refines a citrus fragrance by adding a feeling of freshness, crispness and coolness to create a more natural and more preferred fragrance.

SUMMARY OF THE INVENTION

The inventor of the present invention has conducted extensive investigations and found as a result that optically and chemically pure (−)-n-isopulegol is odorless and that the optically and chemically pure (−)-n-isopulegol imparts a feeling of freshness, crispness, and coolness to a citrus note.

The present invention relates to a method for purifying isopulegol comprising deep cooling isopulegol mainly composed of (−)-n-isopulegol in a deep cooling solvent mainly comprising acetone to obtain (−)-n-isopulegol having a chemical purity of not less than 99.7% by weight and an optical purity of not less than 99.7%e.e.

The present invention further relates to a citrus perfume composition containing the (−)-n-isopulegol obtained by the above purification method, preferably in an amount of from 3 to 30% by weight.

DETAILED DESCRIPTION OF THE INVENTION

Isopulegol has three asymmetric carbon atoms and includes four geometric isomers (n-form, neo-form, iso-form, and neoiso-form) and eight optical isomers. The eight optical isomers are shown below.

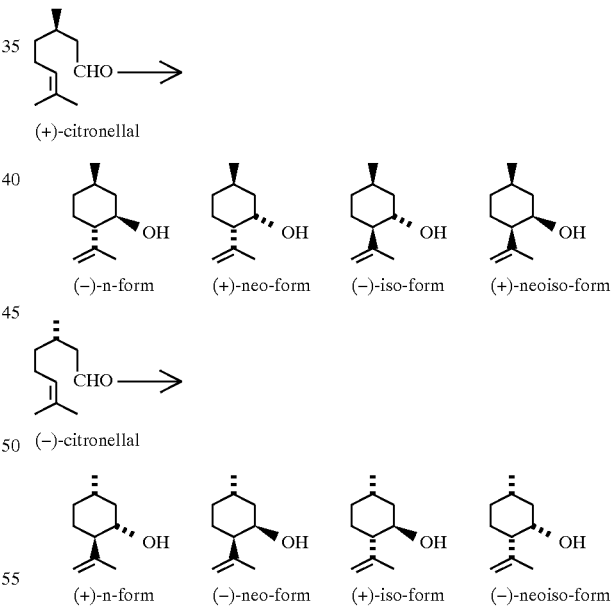

As previously described, isopulegol that has conventionally been used as a perfume component is a mixture of the eight optical isomers mainly comprising (−)-n-isopulegol which is synthesized by cyclization of (+)-citronellal obtained from citronella oil and having an optical purity of 80 to 85%e.e. (d-form: 90 to 92.5%; l-form: 10 to 7.5%) or (+)-citronellal obtained by asymmetric isomerization of geranyl diethylamine using an Rh-BINAP catalyst and having an optical purity of 97.5 to 98%e.e. (d- form: 98.75 to 99%; l-form: 1.25 to 1.0%).

In menthol synthesis according to the above Takasago Process, (−)-n-isopulegol having a chemical purity of 97.1% by weight and an optical purity of 97.5%e.e. is obtained as an intermediate. This compound can be purified by deep cooling in a petroleum hydrocarbon, followed by recrystallization once or twice, and followed by distillation to give (−)-n-isopulegol having an optical purity of not lower than 99%e.e. and a chemical purity of 99 to 99.7% by weight. The thus purified compound still has a relatively mild, minty herbaceous, and bitter sweet scent and can be used as a perfume component.

There are reports on optically pure (−)-n-isopulegol obtained by, for example, repeated recrystallization in petroleum ether (*Perfume & Essential O.R.*, p. 365 (1968)) or recrystallization of a magnesium salt of isopulegol phthalate (*J. Chem. Soc.*, p. 1248 (1920)), but no mention of the fragrance of the thus purified compound is made in the reports.

Assuming that the smell of (−)-n-isopulegol is ascribed to less than 0.3% by weight of impurity, the inventor aimed at examining the fragrance of (−)-n-isopulegol having a chemical and optical purity of 99.7% by weight or higher. For this purpose, the inventor purified the above-mentioned (−)-n-isopulegol having an optical purity of not lower than 99%e.e. and a chemical purity of 99 to 99.7% by weight by cooling at −30° to −35° C. while stirring in twice (vol/wt) as much petroleum ether as the isopulegol, separating the precipitated crystals by centrifugation, and repeating the same operation (deep cooling) six times to obtain (−)-n-isopulegol having a chemical purity of 100% by weight and an optical purity of 100%e.e. ($[\alpha]_D^{25}=-22.1°$). As a result, it was surprisingly revealed that the pure (−)-n- isopulegol is odorless, giving off no minty and herbaceous odor which has hitherto been considered essential to isopulegol, but only possesses refreshing stimulation giving a feeling of coolness.

In order to identify the perfuming components of the unpurified (−)-n-isopulegol, the mother liquor was subjected to precise fractional distillation (rectification) on a 40-plate Heli-Pack distillation tower. Gas chromatography of the distillate lent confirmation to the presence of impurities which are by-produced in cyclization of citronellal, such as 3,8-paramenthadiene, 2,8-paramenthadiene, 3-methylcyclohexanol, menthone, and isomenthone, revealing that these compounds are the main cause of what has been called fragrance of isopulegol.

Since the above-mentioned purification method consisting of recrystallization many times is costly for industrial application, the inventor has studied an economical method for synthesizing chemically and optically pure odorless (−)-n-isopulegol.

First of all, rectification of (−)-n-isopulegol having an optical purity of 97.5%e.e. and a chemical purity of 97.5% by weight was attempted by using a distillation tower, such as a Heli-Pack column having 100 theoretical plates. It was confirmed that the thus purified (−)-n- isopulegol has a reduced and yet perceivable odor characteristic of conventionally available isopulegol and that mere distillation does not render isopulegol odorless.

As a next approach, the inventor attempted recrystallization using a variety of solvents for deep cooling and found acetone especially excellent as a deep cooling solvent as demonstrated in Example 3 hereinafter described.

Thus, it was found that deep cooling using acetone as a solvent affords needle-shaped particulate crystals having a high bulk density which neatly settle to the bottom of a reaction container without adhering to the container or a stirrer. If, on the other hand, other solvents like petroleum ether are used as a solvent, it turned out that the precipitated crystals are light and fluffy needle-like crystals, which easily adhere to the reaction container or a stirrer only to attain a poor separation efficiency in the subsequent centrifugation. Therefore, recrystallization using these solvents is not efficient for removing a trace amount of the impurity.

Since the crystals obtained by a single deep cooling operation according to the present invention have high purity both chemically and optically, a final product ((−)-n-isopulegol) obtained therefrom simply by centrifugal separation followed by cutting the initial fraction by means of a distillation tower is optically and chemically pure as analyzed by gas chromatography, having an optical purity as high as 99.7%e.e. or even higher and a chemical purity as high as 99.7% by weight or even higher, and has no odor but pleasant refreshing stimulation.

When deep cooling is conducted using an oxygen-containing compound, such as ethyl acetate, methanol, ethanol, tetrahydrofuran, methyl ethyl ketone, dipropyl ether, and diethyl ether, as a solvent, the purity of isopulegol can be increased slightly. Acetone is the most preferred solvent.

Acetone is preferably used in an amount 1 to 5 times, still preferably 1.5 to 3.0 times, in terms of volume per weight, as much as the isopulegol.

A minor proportion (preferably at most 30% by weight) of acetone may be replaced with the aforesaid oxygen-containing solvent.

The deep cooling temperature preferably ranges from −20° to −60° C., still preferably from −25° to −50° C.

After the deep cooling, the crystals are collected by centrifugation and then subjected to rectification with, for example, a 5 to 40-plate Heli-Pack distillation tower to obtain a final product for the market. Where isopulegol to be purified is subjected to rectification before deep cooling, the crystals may be subjected to single distillation to obtain a final product.

The thus obtained odorless and chemically and optically pure (−)-n-isopulegol having a chemical and optical purity of not lower than 99.7% can be used to impart a feeling of freshness, crispness, and coolness to a citrus fragrance.

The citrus fragrance which can be used in the present invention includes those of lemons, oranges, mandarins, litchis, bergamot, and grapefruits.

(−)-n-Isopulegol according to the present invention is used in a citrus perfume composition in a proportion of 3 to 30% by weight, preferably 5 to 20% by weight. If the proportion is less than 3% by weight, the perfume composition tends to lack freshness. If it exceeds 30% by weight, the top note of the composition tends to be unbalanced.

The present invention is now illustrated in greater detail with reference to Examples, but it should be understood that the present invention is not limited thereto.

EXAMPLE 1

Purification of (−)-n-Isopulegol (−)-n-Isopulegol which is an intermediate for the synthesis of menthol was obtained by the above-described Takasago Process. The intermediate has a chemical purity of 97.1% [impurity composition: 0.9% iso-form, 1.7% neo-form, not more than 0.1% neoiso-form, and not more than 0.1% others (3,8-paramenthadiene and other several compounds)] and an optical purity of 97.5%e.e. ($[\alpha]_D^{25}=-20.90°$) as analyzed by gas chromatography (GC) under the following conditions and has a herbaceous minty fragrance.

Conditions of GC:

Column: Chiraldex CB (25 m×0.25 mm diameter), produced by Chromato Pack

He pressure: 1 kg/cm$^2$

Temperature: elevated at a rate of 2° C./min from 60° C. up to a constant temperature of 190°

Retention time for (+)-n-compound: 27.9 min

Retention time for (−)-n-compound: 28.3 min

In a 3 l-volume 4-necked container for deep cooling was put 500 g of the above-mentioned (−)-n-isopulegol, and 1500 ml of acetone was added thereto. The mixture was cooled to −40° C. in a nitrogen stream, and the precipitated solid was separated by centrifugation to obtain 367 g of crystals.

The crystals were melted and distilled in a 40-plate Heli-Pack tower to obtain 305 g of (−)-n-isopulegol (64.5° C./1 mmHg) which was found to be 100% pure both optically and chemically ($[\alpha]_D^{25}=-22.1°$) as analyzed by gas chromatography. The crystals were odorless and had a refreshing feeling of coolness.

EXAMPLE 2

Purification of (−)-n-Isopuleqol (−)-n-Isopulegol having a purity of 69% (as measured by gas chromatography) was synthesized from (+)-citronellal of citronella oil origin (optical purity: 81%e.e.) by the process of using silica gel (U.S. Pat. No. 3,218,361). In a 3 l-volume 4-necked container for deep cooling was put 800 g of the (−)-n-isopulegol in a nitrogen stream, 1,500 ml of n-heptane was added to the container, and the mixture was cooled to −45° C. The precipitated crystals were separated by centrifugation to collect 480 g of crystals having a chemical purity of 94% and an optical purity of 95%e.e.

The crystals (450 g) were melted and placed in a 2 l-volume 4-necked container for deep cooling in a nitrogen stream, and 1200 ml of acetone was added thereto. The mixture was cooled to −40° C. in a nitrogen stream, and the precipitated solid was separated by centrifugation to obtain 304 g of crystals having a chemical purity of 99.6% and an optical purity of 99.9%e.e.

The crystals (300 g) were melted and put in a 1 l-volume 4-necked container for deep cooling in a nitrogen stream, and 400 ml of acetone was added thereto. The mixture was cooled to −35° C. in a nitrogen stream, and the precipitated solid was separated by centrifugation to obtain 233 g of crystals having a chemical purity of 100% and an optical purity of 100%e.e.

The resulting crystals (220 g) were melted and distilled in a Widmer spiral to obtain 190 g of (−)-n- isopulegol (64.5° C./1 mmHg) which was found to be 100% pure both optically and chemically ($[\alpha]_D^{25}=-22.1°$) as analyzed by gas chromatography. The crystals were odorless and had a refreshing feeling of coolness.

EXAMPLE 3

(−)-n-Isopulegol was purified in the same manner as in Example 1, except for changing acetone with various other solvents. The physical properties of the (−)-n-isopulegol crystals obtained by deep cooling are shown in Table 1 below. Further, the odor of the resulting (−)-n-isopulegol crystals was organoleptically evaluated by 30 panel members.

TABLE 1

| Solvent | Optical Purity (% e. e.) | Chemical Purity (%) | Odor | Judgement |
|---|---|---|---|---|
| Heptane | 99.7 | 99.0 | isopulegol odor | no good |
| Hexane | 99.6 | 98.9 | " | " |
| Toluene | 99.7 | 99.2 | " | " |
| Methanol | 99.9 | 99.6 | slight isopulegol odor | acceptable |
| Ethanol | 99.8 | 99.6 | " | " |
| Tetrahydrofuran | 99.9 | 99.6 | " | " |
| Ethyl acetate | 99.9 | 99.6 | " | " |
| Methyl ethyl ketone | 99.9 | 99.6 | " | " |
| Acetone | 100.0 | 100.0 | odorless | excellent |

It is seen from Table 1 that acetone gives the most satisfactory results.

EXAMPLE 4

Formulation of Citrus Fragrance

A fresh lime cologne having each of the formulations shown in Table 2 was prepared. The (−)-n-isopulegol content in each composition was 10% by weight.

TABLE 2

|  | Formulation 1 | Formulation 2 | Formulation 3 |
|---|---|---|---|
| Bergamot oil | 150 | 150 | 150 |
| Grapefruit oil | 10 | 10 | 10 |
| Lemon oil | 50 | 50 | 50 |
| Lime oil (Mexico) | 120 | 120 | 120 |
| Lime oil (Mexico) | 10 | 10 | 10 |
| Terpeneless mandarin oil | 10 | 10 | 10 |
| Orange oil (Guinea) | 50 | 50 | 50 |
| Lemon oil TP FL-82 | 500 | 500 | 500 |
| Conventional (−)-n-isopulegol | 0 | 100 | 0 |
| (−)-n-Isopulegol obtained in Example 1 | 0 | 0 | 100 |
| Dipropylene glycol | 100 | 0 | 0 |
| Total | 1000 | 1000 | 1000 |

As a result of organoleptic evaluation by 30 panel members, all the panel members judged that Formulation 2 had its fragrance unbalanced by the odor of the conventional (−)-n-isopulegol and that Formulation 1 containing no isopulegol was much better. Further, they all preferred Formulation 3 containing the (−)-n-isopulegol obtained in Example 1 to Formulation 1, indicating that the former had enhanced freshness with a character closer to a natural fresh lime.

EXAMPLE 5

Formulation of Citrus Fragrance

A fresh neroli type cologne which suits all tastes was prepared according to Formulation 4 shown below. The (−)-n-isopulegol content in the composition was 10% by weight.

| Formulation 4: | |
| --- | --- |
| Petigrain oil | 100 |
| Lemon oil | 250 |
| Orange oil | 100 |
| Mandarin oil | 50 |
| Bergamot oil | 300 |
| Nerol | 50 |
| Lavandin oil | 50 |
| (−)-n-Isopulegol obtained in Example 2 | 100 |
| Total | 1000 |

According to the present invention, (−)-n-isopulegol of extremely high purity can be obtained by using acetone as a solvent for deep cooling. Incorporation of the isopulegol obtained by the purification method of the present invention which is odorless and has chemical and optical purity of not less than 99.7% provides a citrus perfume composition having a feeling of freshness, crispness, and coolness and meeting all the taste.

While the invention has been described in detail and with reference to specific examples thereof, it will be apparent to one skilled in the art that various changes and modifications can be made therein without departing from the spirit and scope thereof.

What is claimed is:

1. A citrus perfume composition comprising citrus perfume components which are blended with odorless (−)-n-isopulegol, said citrus perfume composition containing (−)-n-isopulegol having a chemical purity of not less than 99.7% by weight and an optical purity of not less than 99.7% e.e. prior to use in said perfume composition and in which the (−)-n-isopulegol component of the citrus perfume composition is not less than 99.7 (−)-n-isopulegol by weight based on isopulegol and its geometric and optical isomers and having an optical purity of not less than 99.7% e.e. which is obtained by deep cooling isopulegol mainly composed of (−)-n-isopulegol in a solvent for deep cooling mainly comprising acetone.

2. A citrus perfume composition containing said odorless (−)-n-isopulegol having a chemical purity of not less than 99.7% by weight and an optical purity of not less than 99.7%e.e. which is obtained by deep cooling isopulegol mainly composed of (−)-n-isopulegol in a solvent for deep cooling mainly comprising acetone, wherein (−)-n-isopulegol is present in an amount from 3 to 30% by weight.

* * * * *